United States Patent [19]

Yamamoto et al.

[11] 4,247,554
[45] Jan. 27, 1981

[54] METHOD FOR THE PREVENTION OF GASTRO-INTESTINAL ULCER CAUSED BY A NON-STEROIDAL ANTI-INFLAMMATORY AGENT

[75] Inventors: Hisao Yamamoto, Osaka; Toshiaki Komatsu, Takarazuka; Hiroshi Awata, Toyonaka, all of Japan

[73] Assignee: Sumitomo Chemical Company, Limited, Osaka, Japan

[21] Appl. No.: 795,887

[22] Filed: May 11, 1977

Related U.S. Application Data

[63] Continuation of Ser. No. 589,573, Jun. 23, 1975, abandoned.

[51] Int. Cl.³ .................................................. A61K 31/505
[52] U.S. Cl. .................................................. 424/251
[58] Field of Search .................................. 424/251, 10

[56] References Cited

U.S. PATENT DOCUMENTS

| 3,712,892 | 1/1973 | Inaba et al. | 260/251 QB |
| 3,812,118 | 5/1974 | Yamamoto et al. | 260/247.1 |
| 3,859,237 | 1/1975 | Inaba et al. | 260/251 QB |
| 3,937,801 | 2/1976 | Lippmann | 424/10 |

OTHER PUBLICATIONS

Cutting–Handbook of Pharmacology, 4th Ed., pp. 618–625, (1969).

Primary Examiner—Frederick E. Waddell
Attorney, Agent, or Firm—Stevens, Davis, Miller & Mosher

[57] ABSTRACT

A method for preventing gastro-intestinal ulcer caused by a non-steroidal anti-inflammatory agent, which comprises administering an effective amount of a quinazolinone of the formula,

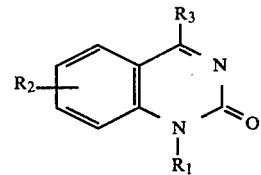

wherein $R_1$ is $C_{1-3}$ alkyl, cyclopropylmethyl or 2,2,2-trifluoroethyl, $R_2$ is halogen, $C_{1-3}$ alkyl or $C_{1-3}$ alkoxy, and $R_3$ is phenyl or thienyl, or a non-toxic pharmaceutically acceptable salt thereof in combination with a pharmaceutically effective amount of the non-steroidal anti-inflammatory agent.

29 Claims, No Drawings

METHOD FOR THE PREVENTION OF GASTRO-INTESTINAL ULCER CAUSED BY A NON-STEROIDAL ANTI-INFLAMMATORY AGENT

This is a continuation of application Ser. No. 589,573 filed June 23, 1975, now abandoned.

This invention relates to a method for preventing gastro-intestinal ulcer caused by a non-steroidal anti-inflammatory agent.

It has been well known that many of non-steroidal anti-inflammatory agents exhibit ulcerogenic activities such as gastric hemorrhage and intestinal perforation (e.g., L. Levy, Chapter 4, Assessment of the toxicity of anti-inflammatory agents, "Anti-inflammatory agents" Chemistry and Phermacology, Volume II (1974) pp. 206–208. Editor, R. A. Scherrer and M. W. Whitehouse, Academic Press, New York). Therefore, these drugs should not be administered to a patient with gastro-intestinal ulcer.

In order to improve the above inconvenience, the present inventors have made various studies and have found that administration of a quinazolinone in combination with a non-steroidal anti-inflammatory agent possessing ulcerogenic potential, exhibits the remarkable effect for the prevention of gastro-intestinal ulcer caused by the said anti-inflammatory agent, and the effect is markedly observed particularly in the case of intestinal perforation.

Thus, it is an object of the present invention to provide a method for preventing gastro-intestinal ulcer caused by a non-steroidal anti-inflammatory agent.

Another object is to provide a pharmaceutical composition for preventing such ulcer. Other objects will be apparent from the following description.

In order to accomplish these objects, the present invention provides a method for preventing gastro-intestinal ulcer in mammals caused by a non-steroidal anti-inflammatory agent, which comprises administering an effective amount of a quinazolinone of the formula [I],

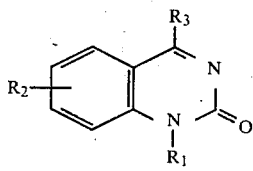

wherein $R_1$ is $C_{1-3}$ alkyl, cyclopropylmethyl or 2,2,2-trifluoroethyl, $R_2$ is halogen. $C_{1-3}$ alkyl or $C_{1-3}$ alkoxy, and $R_3$ is phenyl or thienyl, or a non-toxic pharmaceutically acceptable salt thereof, in combination with a pharmaceutically effective amount of the said anti-inflammatory agent, and also provides a pharmaceutical composition for preventing gastro-intestinal ulcer caused by a non-steroidal anti-inflammatory agent when administered orally to mammals, comprising a pharmaceutically acceptable carrier or diluent and an effective amount of the quinazolinone of the formula [I], or a non-toxic pharmaceutically acceptable salt thereof and an effective amount of the said anti-inflammatory agent.

The quinazolinones employed in the present invention are known as anti-inflammatory and analgesic agents with low toxicities and are described in the art such as U.S. Pat. Nos. 3,712,892, 3,859,237; British Pat. Nos. 1,251,600, 1,307,202; Arzneim-Forsch 23, 1266 (1973); and Arzneim-Forsch 22, 1958 (1972).

In a preferred embodiment of the present invention, examples of the quinazolinone include 1-cyclopropylmethyl-4-phenyl-6-chloro-2-(1H)-quinazolinone, 1-cyclopropylmethyl-4-phenyl-6-methoxy-2(1H)-quinazolinone, 1-(2,2,2-trifuloroethyl)-4-phenyl-6-chloro-2(1H)-quinazolinone and 1-(2,2,2-trifluoroethyl)-4-phenyl-6-methoxy-2(1H)-quinazolinone.

The non-steroidal anti-inflammatory agents employed in the present invention are, for example, indolylacetic acid derivatives such as indomethacin, 1-(3,4-methylenedioxybenzoyl)-5-methoxy-2-methyl-3-indolylacetic acid and 1-cinnamoyl-5-methoxy-2-methyl-3-indolylacetic acid; anthranilic acid derivatives such as mefenamic acid and flufenamic acid; and pyrazole derivatives such as phenylbutazone.

According to the method of the present invention, gastro-intestinal ulcer caused by indomethacin, mefenamic acid, flufenamic acid and phenylbutazone are particularly prevented. Both components of the drugs may be administered simultaneously or sequentially. However, they are preferably administered orally to mammals simultaneously.

Practically, they may be given in a single pharmaceutical composition containing the both components and a pharmaceutically acceptable carrier or diluent.

The compositions are above all used in the form of pharmaceutical preparations for human and veterinary medicine, appropriate for enteral administration. Possible excipients are those which do not react with both components of the drugs mentioned above, for example water, gelatine, lactose, starch, stearic acid, magnesium stearate, talc, white petroleum jelly, vegetable oils, alcohol, benzyl alcohol, gums, polyalkylene glycols, or other known excipients for medicines. The pharmaceutical preparations may, for example, be in the form of tablets, powder, dragees, sugar-coated tablets, capsules, suppositories, liquids, elixirs, emulsions, suspensions, syrups, waters or the like.

If desired, they are sterilized and/or contain auxiliary substances such as preservatives, stabilizers, wetting agents, detergents or buffers.

The preparations are formulated by the usual methods.

A weight ratio of the quinazolinone of the formula [I] or its salt to the non-steroidal anti-inflammatory agent is preferably within a range of from about 20:1 to about 1:5.

The effective amount of the quinazolinone in such useful compositions or preparations is variable according to the amount of the non-steroidal anti-inflammatory agent which is generally employed at the doses lower than or equal to the recommended doses. The features of the present invention will now be discussed in greater details for the purpose of illustration, but it is not intended to be interpreted as limiting.

Experiment 1

Inhibitory effect of the quinazolinone derivatives on the indomethacin-induced intestinal perforation in rats.

Male rats of HLA-Wistar strain weighing 200 to 230 g were employed. Test compounds suspended in 5% gum arabic were orally given in a volume of 1 ml per 100 g body weight.

Body weight gain, and intestinal perforation were observed on day 5 after treatment.

Thus obtained results are demonstrated in Table 1.

Table 1

Anti-ulcerogenic effect of quinazolinone derivatives on indomethacin-induced intestinal perforation in rats

| Indomethacin dose (mg/kg) | Quinazolinone derivative | Dose (mg/kg) | Dead/ Treated | Body wt. gain g ± SE | Intestinal perforation[*1] | | | |
|---|---|---|---|---|---|---|---|---|
| | | | | | − | + | ++ | +++ |
| 10 | | 0 | 1/6 | −21.2 ± 7.4 | 0 | 0 | 0 | 6 |
| 10 | 1-Cyclopropylmethyl-4-phenyl-6-methoxy-2(1H)-quinazolinone | 10 | 0/6 | 13.7* ± 13.5 | 1 | 1 | 1 | 3 |
| 10 | | 20 | 0/6 | 34.8** ± 2.7 | 1 | 1 | 3 | 1 |
| 10 | | 50 | 0/6 | 35.3** ± 3.5 | 4 | 2 | 0 | 0 |
| 10 | 1-Cyclopropylmethyl-4-phenyl-6-chloro-2(1H)-quinazolinone | 20 | 0/6 | 38.3** ± 3.6 | 0 | 2 | 1 | |
| 10 | | 50 | 0/6 | 40.8** ± 3.0 | 5 | 1 | 0 | 0 |
| 10 | 1-(2,2,2-Trifluoroethyl)-4-phenyl-6-chloro-2(1H)-quinazolinone | 20 | 0/6 | 34.7* ± 7.5 | 0 | 2 | 2 | 2 |
| 10 | | 50 | 0/6 | 46.0** ± 1.7 | 5 | 1 | 0 | 0 |
| 10 | 1-Methyl-4-phenyl-6-chloro-2(1H)-quinazolinone | 20 | 0/6 | 9.3* ± 8.1 | 0 | 1 | 1 | 4 |
| 10 | | 50 | 0/6 | 21.8* ± 12.0 | 0 | 2 | 2 | 2 |
| 10 | | 100 | 0/6 | 43.5** ± 4.1 | 3 | 0 | 0 | |
| 10 | 1-Ethyl-4-phenyl-6-chloro-2(1H)-quinazolinone | 20 | 0/6 | 24.5* ± 5.9 | 0 | 3 | 0 | 3 |
| 10 | | 50 | 0/6 | 41.3** ± 2.9 | 2 | 2 | 0 | 2 |
| 10 | | 100 | 0/6 | 43.7** ± 2.3 | 4 | 2 | 0 | 0 |
| 10 | 1-Cyclopropylmethyl-4-phenyl-7-methyl-2(1H)-quinazolinone | 50 | 0/6 | 39.3** ± 3.9 | 2 | 2 | 1 | 1 |
| 10 | 1-Cyclopropylmethyl-4-phenyl-7-methyoxy-2(1H)-quinazolinone | 50 | 0/6 | 36.8** ± 4.1 | 1 | 2 | 2 | 1 |
| 10 | 1-Cyclopropylmethyl-4-(2-thienyl)-6-methoxy-2(1H)-quinazolinone | 50 | 0/6 | 33.7** ± 5.1 | 1 | 2 | 2 | 1 |
| 10 | 1(2,2,2-Trifluoroethyl)-4-phenyl-6-methoxy-2(1H)-quinazolinone | 50 | 0/6 | 46.0** ± 2.9 | 5 | 1 | 0 | 0 |

\*P < 0.05
\*\*P < 0.01
[*1] −: negative,
+: slight,
++: moderated,
+++: severe

As is apparent from the above table, the intestinal perforations caused by the indolylacetic acid derivatives having gastro-intestinal ulceration effect are dramatically prevented when the quinazolinone derivative of the present invention is used in combination with the indolylacetic acid, and as the result the suppress of the body weight gain and mortality caused by indomethacin are recovered considerably. Indomethacin produced severe intestinal perforation at the dose level of 10 mg/kg, while a series of quinazolinone derivatives of this invention (20 to 50 mg/kg) markedly inhibited the occurrence of intestinal perforation when they were administered by combining with indomethacin.

Experiment 2

Inhibitory effect of the compound according to the present invention on the indomethacin-induced intestinal perforation in rats when administered for 2 weeks.

This experiment was performed in the similar method to that in Exp. 1 except for duration of treatment.

Table 2

Anti-ulcerogenic effect of quinazolinone derivatives on indomethacin-induced intestinal perforation in rats when administered for 2 weeks

| Daily dose mg/kg (po) | | Dead/ Treated | Body wt. gain g ± SE | Intestinal perforation[*1] | | | |
|---|---|---|---|---|---|---|---|
| Indomethacin | 1-Cyclopropylmethyl-4-phenyl-6-methoxy-2(1H)-quinazolinone | | | − | + | ++ | +++ |
| 0 | 0 | 0/6 | 104 ± 5 | 6 | 0 | 0 | 0 |
| 2 | 0 | 0/6 | 98 ± 3 | 5 | 1 | 0 | 0 |
| 4 | 0 | 2/6 | 94 ± 5 | 2 | 1 | 1 | 2 |
| 4 | 4 | 0/6 | 108 ± 7 | 3 | 1 | 1 | 1 |
| 4 | 8 | 0/6 | 104 ± 5 | 4 | 2 | 0 | 0 |
| 4 | 20 | 0/6 | 114 ± 4 | 4 | 2 | 0 | 0 |
| 4 | 40 | 0/6 | 97 ± 4 | 6 | 0 | 0 | 0 |
| 4 | 80 | 0/6 | 96 ± 3 | 6 | 0 | 0 | 0 |
| 0 | 80 | 0/6 | 99 ± 5 | 6 | 0 | 0 | 0 |

[*1] see the legend in Table 1

As is apparent from the above table, the intestinal perforations in rats caused by these indolylacetic acids are also prevented when administered for 2 weeks as well as administered once. And the compound 1-cyclopropylmethyl-4-phenyl-6-methoxy-2(1H)-quinazolinone inhibited the occurrence of intestinal perforation induced with indomethacin. The inhibition was partial in case of 1:1 to 1:2, but complete when the ratio was 1:5 to 1:10.

Experiment 3

Inhibitory effect of the quinazolinone derivative on the intestinal perforation induced with indolylacetic acid derivatives in rats This experiment was performed according to the similar method as mentioned in Experiment 1.

As is clear from the above table, the quinazolinone compound of the present invention has an excellent anti-ulcerogenic effect on intestinal perforation in rats induced by phenylbutazone or mefenamic acid when the former is administered in combination with the latter.

Experiment 5

Effects of the quinazolinone derivative on the anti-inflammatory effect of non-steroidal anti-inflammatory agents Anti-inflammatory effect was determined by the carrageenin-induced edema inhibition test according to Winter's method.

Six to twelve male rats of HLA-Wistar strain weighing 150 to 170 g per group were used. 0.05 ml of 1%

Table 3

Anti-ulcerogenic effect of quinazolinone derivatives on anti-inflammatory indolylacetic acid derivatives-induced intestinal perforation in rats

| | Dose (mg/kg) | | Body wt. | Intestinal perforation*[1] | | | |
|---|---|---|---|---|---|---|---|
| Indolylacetic acid derivative | 1-Cyclopropylmethyl-4-phenyl-6-methoxy-2(1H)-quinazolinone | Dead/Treated | gain g ± SE | − | + | ++ | +++ |
| (A) | 200 | 0 | 0/6 | −14.2 ± 10.2 | 0 | 0 | 0 | 6 |
| | 200 | 100 | 0/6 | 47.7 ± 3.3** | 0 | 3 | 0 | 3 |
| | 200 | 200 | 0/6 | 45.3 ± 1.5** | 2 | 3 | 1 | 0 |
| | 200 | 400 | 0/6 | 42.7 ± 1.8** | 6 | 0 | 0 | 0 |
| | 400 | 0 | 1/6 | −38.6 ± 9.4 | 0 | 0 | 0 | 6 |
| | 400 | 100 | 0/6 | −8.2 ± 18.5* | 0 | 2 | 0 | 4 |
| (B) | 200 | 0 | 0/6 | 9.5 ± 9.6 | 0 | 0 | 1 | 5 |
| | 200 | 100 | 0/6 | 38.7 ± 8.5* | 0 | 4 | 0 | 2 |
| | 200 | 200 | 0/6 | 50.5 ± 2.5** | 4 | 2 | 0 | 0 |
| | 200 | 400 | 0/6 | 46.2 ± 2.0** | 6 | 0 | 0 | 0 |
| | 400 | 0 | 4/6 | −31.5 ± 1.5 | 0 | 0 | 0 | 6 |
| | 400 | 100 | 0/6 | −25.5 ± 6.2 | 0 | 0 | 0 | 6 |

*[1] see the legend in Table 1
(A): 1-cinnamoyl-5-methoxy-2-methyl-3-indolylacetic acid
(B): 1-(3,4-methylenedioxybenzoyl)-5-methoxy-2-methyl-3-indolylacetic acid As seen in Table 3, the quinazolinone derivative of the present invention inhibited the intestinal perforation induced by the other anti-inflammatory indolylacetic acid derivatives than indomethacin.

Experiment 4

Inhibitory effect of the quinazolinone derivative on the intestinal perforation induced by anti-inflammatory agents other than indomethacin.

The similar method as employed in Experiment 1 was used. Intestinal perforating activity of phenylbutazone or mefenamic acid was markedly reversed with the compound of the present invention. The results obtained are shown in Table 4.

carrageenin suspension in sterile saline solution was injected into plantar tissue of the right hind paw. Test compounds suspended in 5% gum arabic were administered orally 1 hour before the carrageenin injection and the foot volume was determined 4 hours after the carrageenin injection.

Table 5

Effect of the quinazolinone derivative on the anti-inflammatory activities of indomethacin or phenylbutazone in carrageenin-induced edema test in rats Inhibition of edema (%)
Indomethacin Table 4

Anti-ulcerogenic effect of the compound on phenylbutazone or mefenamic acid-induced intestinal perforation in rats

| | Dose (mg/kg) | | Body wt. | Intestinal perforation | | | |
|---|---|---|---|---|---|---|---|
| Anti-inflammatory agent | 1-Cyclopropylmethyl-4-phenyl-6-methoxy-2(1H)-quinazolinone | Dead/Treated | gain g ± SE | − | + | ++ | +++ |
| Phenyl-butazone | 400 | 0 | 0/6 | −6.5 ± 10.9 | 0 | 1 | 2 | 3 |
| | " | 100 | 0/6 | 20.0 ± 3.1 | 2 | 4 | 0 | 0 |
| | " | 200 | 0/6 | 46.7* ± 4.2 | 6 | 0 | 0 | 0 |
| | " | 400 | 0/6 | 47.3* ± 4.7 | 6 | 0 | 0 | 0 |
| Mefenamic acid | 400 | 0 | 0/6 | 24.5 ± 5.4 | 0 | 0 | 1 | 5 |
| | " | 100 | 0/6 | 20.0 ± 3.1 | 0 | 4 | 2 | 0 |
| | " | 200 | 0/6 | 42.5* ± 3.0 | 1 | 4 | 1 | 0 |
| | " | 400 | 0/6 | 45.2* ± 4.2 | 6 | 0 | 0 | 0 |

*$p < 0.05$

Table 5-continued
Effect of the quinazolinone derivative
on the anti-inflammatory activities
of indomethacin or phenylbutazone in
carrageenin-induced edema test in rats

|  | Dose (mg/kg) | dose (mg/kg) | | |
| --- | --- | --- | --- | --- |
|  |  | 0 | 1 | 2 |
| 1-Cyclopropylmethyl-4- | 0 | — | 13.1 | 36.1 |
| phenyl-6-methoxy-2(1H)- | 5 | 14.9 | 29.8 | — |
| quinazolinone | 10 | 31.5 | — | 47.2 |

|  | Dose (mg/kg) | Inhibition of edema (%) Phenylbutazone dose (mg/kg) | | |
| --- | --- | --- | --- | --- |
|  |  | 0 | 50 | 100 | 200 |
|  | 0 | — | 26.1 | 31.5 | 45.7 |
| 1-Cyclopropylmethyl- | 50 | 32.6 | — | 31.5 | — |
| 4-phenyl-6-methoxy- | 100 | 42.4 | 40.2 | 37.0 | 46.2 |
| 2(1H)-quinazolinone | 200 | 56.5 | — | 39.1 | — |

As clearly indicated in Table 5, anti-inflammatory effect with simultaneous administration of indomethacin or phenylbutazone and the quinazolinone derivative was additive but not antagonistic. Therefore, it is concluded that the quinazolinone derivatives do not inhibit anti-inflammatory effects of other non-steroidal anti-inflammatory agents, but act additively.

What is claimed is:

1. A method for preventing gastro-intestinal ulcer in mammals undergoing anti-inflammatory treatment with a non-steroidal anti-inflammatory agent, which comprises orally administering a gastro-intestinal ulcer preventing effective amount of a quinazolinone of the formula,

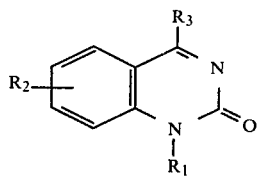

wherein $R_1$ is $C_{1-3}$ alkyl, cyclopropylmethyl or 2,2,2-trifluoroethyl, $R_2$ is halogen, $C_{1-3}$ alkyl or $C_{1-3}$ alkoxy, and $R_3$ is phenyl or thienyl, or a non-toxic pharmaceutically acceptable salt thereof, in combination with an anti-inflammatorily effective amount of the anti-inflammatory agent.

2. The method according to claim 1, wherein the quinazolinone is 1-cyclopropylmethyl-4-phenyl-6-chloro-2(1H)-quinazolinone.

3. The method according to claim 1, wherein the quinazolinone is 1-cyclopropylmethyl-4-phenyl-6-methoxy-2(1H)-quinazolinone.

4. The method according to claim 1, wherein the quinazolinone is 1-(2,2,2,-trifluoroethyl)-4-phenyl-6-chloro-2(1H)-quinazolinone.

5. The method according to claim 1, wherein the quinazolinone is 1-(2,2,2-trifluoroethyl)-4-phenyl-6-methoxy-2(1H)-quinazolinone.

6. The method according to claim 1, wherein the non-steroidal anti-inflammatory agent is a member selected from the group consisting of indolylacetic acid derivatives, anthranilic acid derivatives and pyrazole derivatives.

7. The method according to claim 6, wherein the indolylacetic acid derivative is a member selected from the group consisting of indomethacin, 1-cinnamoyl-5-methoxy-2-methyl-3-indolylacetic acid and 1-(3,4-methylenedioxybenzoyl)-5-methoxy-2-methyl-3-indolylacetic acid.

8. The method according to claim 6, wherein the anthranilic acid derivative is a member selected from the group consisting of mefenamic acid and flufenamic acid.

9. The method according to claim 6, wherein the pyrazole derivative is phenylbutazone.

10. A pharmaceutical composition for preventing gastro-intestinal ulcer caused by a non-steroidal anti-inflammatory agent when administered orally to mammals, comprising a pharmaceutically acceptable carrier or diluent and a gastro-intestinal ulcer preventing effective amount of a quinazolinone of the formula,

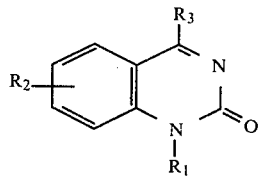

wherein each of $R_1$, $R_2$ and $R_3$ is as defined in claim 1 or a non-toxic pharmaceutically acceptable salt thereof and an anti-inflammatorily effective amount of the said anti-inflammatory agent.

11. The composition according to claim 10, wherein the quinazolinone is 1-cyclopropylmethyl-4-phenyl-6-chloro-2(1H)-quinazolinone.

12. The composition according to claim 10, wherein the quinazolinone is 1-cyclopropylmethyl-4-phenyl-6-methoxy-2(1H)-quinazolinone.

13. The composition according to claim 10, wherein the quinazolinone is 1-(2,2,2-trifluoroethyl)-4-phenyl-6-chloro-2(1H)-quinazolinone.

14. The composition according to claim 10, wherein the quinazolinone compound is 1-(2,2,2-trifluoroethyl)-4-phenyl-6-methoxy-2(1H)-quinazolinone.

15. The composition according to claim 10, wherein the non-steroidal anti-inflammatory agent is a member selected from the group consisting of indolylacetic acid derivatives, anthranilic acid derivatives and pyrazole derivatives.

16. The composition according to claim 15, wherein the indolylacetic acid derivative is a member selected from the group consisting of indomethacin, 1-cinnamoyl-5-methoxy-2-methyl-3-indolylacetic acid and 1-(3,4-methylenedioxybenzoyl)-5-methoxy-2-methyl-3-indolylacetic acid.

17. The composition according to claim 15, wherein the anthranilic acid derivative is a member selected from the group consisting of mefenamic acid and flufenamic acid.

18. The composition according to claim 15, wherein the pyrazole derivative is phenylbutazone.

19. The composition according to claim 10, wherein the weight ratio of the quinazolinone or its salt to the non-steroidal anti-inflammatory agent is within a range of from about 20:1 to about 1:5.

20. A method according to claim 1, wherein the quinazolinone is 1-methyl-4-phenyl-6-chloro-2(1H)-quinazolinone.

21. A method according to claim 1, wherein the quinazolinone is 1-ethyl-4-phenyl-6-chloro-2(1H)-quinazolinone.

22. The method according to claim 1, wherein the quinazolinone is 1-cyclopropylmethyl-4-phenyl-7-methyl-2(1H)-quinazolinone.

23. A method according to claim 1, wherein the quinazolinone is 1-cyclopropylmethyl-4-phenyl-7-methoxy-2(1H)-quinazolinone.

24. A method according to claim 1, wherein the quinazolinone is 1-cyclopropylmethyl-4-(2-thienyl)-6-methoxy-2(1H)-quinazolinone.

25. The composition according to claim 10, wherein the quinazolinone is 1-methyl-4-phenyl-6-chloro-2(1H)-quinazolinone.

26. The composition according to claim 10, wherein the quinazolinone is 1-ethyl-4-phenyl-6-chloro-2(1H)-quinazolinone.

27. The composition according to claim 10, wherein the quinazolinone is 1-cyclopropylmethyl-4-phenyl-7-methyl-2(1H)-quinazolinone.

28. The composition according to claim 10, wherein the quinazolinone is 1-cyclopropylmethyl-4-phenyl-7-methoxy-2(1H)-quinazolinone.

29. The composition according to claim 10, wherein the quinazolinone is 1-cyclopropylmethyl-4-(2-thienyl)-6-methoxy-2(1H)-quinazolinone.

* * * * *